United States Patent [19]

Hahn

[11] Patent Number: 5,114,340

[45] Date of Patent: May 19, 1992

[54] APPARATUS FOR SELECTION OF TOOTH COLOR

[76] Inventor: Rainer Hahn, Hindenburgstrasse 119, D-7300 Esslingen, Fed. Rep. of Germany

[21] Appl. No.: 577,555

[22] Filed: Sep. 5, 1990

[30] Foreign Application Priority Data

Sep. 7, 1989 [DE] Fed. Rep. of Germany ....... 3929737

[51] Int. Cl.$^5$ .............................................. A61C 19/10
[52] U.S. Cl. .................................................... 433/26
[58] Field of Search ................. 433/26, 203.1; 434/98, 434/99, 100

[56] References Cited

U.S. PATENT DOCUMENTS

| | | | |
|---|---|---|---|
| 1,518,608 | 12/1924 | Short | 433/26 |
| 3,405,446 | 10/1968 | Wiener | |
| 3,507,042 | 4/1970 | Hana | |
| 3,748,741 | 7/1973 | Yerkes, Jr. | 433/203.1 |
| 4,115,922 | 9/1978 | Alderman | |
| 4,382,784 | 5/1983 | Freller | 433/26 |
| 4,618,325 | 10/1986 | Appelle | 433/26 |
| 4,620,841 | 11/1986 | Farrell et al. | 433/26 |
| 4,793,805 | 12/1988 | Pitre | 433/26 |

FOREIGN PATENT DOCUMENTS

| | | |
|---|---|---|
| 0147232 | 7/1985 | European Pat. Off. . |
| 0234945 | 9/1987 | European Pat. Off. . |
| 2641740 | 3/1978 | Fed. Rep. of Germany . |
| 3429927 | 2/1986 | Fed. Rep. of Germany . |
| 3503084 | 7/1986 | Fed. Rep. of Germany . |
| 3517344 | 11/1986 | Fed. Rep. of Germany . |
| 3523982 | 1/1987 | Fed. Rep. of Germany . |
| 3713491 | 10/1987 | Fed. Rep. of Germany . |
| 3618153 | 12/1987 | Fed. Rep. of Germany . |
| 8809755 | 11/1988 | Fed. Rep. of Germany . |
| 3731254 | 4/1989 | Fed. Rep. of Germany . |

Primary Examiner—Cary E. O'Connor
Attorney, Agent, or Firm—Cushman, Darby & Cushman

[57] ABSTRACT

An apparatus is provided for the selection of a tooth color for a dental prostheses in which an exact adaptation of the colors or color distribution of a dental prosthesis to a particular structural condition in a patient can be achieved. The apparatus, a platelet color specimen, has at least one lateral edge concavely curved towards a center region of the platelet. The platelet color specimen is on the order of magnitude of only a width of a tooth, and can be placed contiguous with the surface and edge of all exposed portions of a tooth. The platelet color specimen also exhibits only a single color corresponding to enamel, dentin or dental neck which allows for an exact adaptation to a particular patient.

35 Claims, 5 Drawing Sheets

APPARATUS FOR SELECTION OF TOOTH COLOR

BACKGROUND OF THE INVENTION

The invention is relative to an apparatus for the selection of a tooth color for the manufacture of dental prostheses, with several plate-like color specimens which exhibit at least one curved section.

The color of an individual tooth is not distributed evenly and uniformly. The color, brightness and transparency decrease from the cutting edge or the masticatory surface of a tooth to the dental neck. The enamel exhibits a whitish-bluish color and the dentin, yellowish to brownish color tones. The dental neck and the root element are likewise of a yellowish-brownish color but usually darker than the corresponding dentin. The canines are generally somewhat darker than the other teeth.

The color shades of teeth can be very different in different individuals. In addition, inclusions of color can frequently be found on individual teeth, wherein the inclusions are shaded darker or brighter than the immediate surroundings. Finally, teeth become darker and loose translucency as a person ages.

In the restoration of a tooth or of a set of teeth, the tooth color in particular, in addition to the functional shaping, form, size and surface of a tooth, must be correctly selected. A tooth restoration should not only fit harmoniously into the arc of the teeth but it should also be adapted in its course of colors to the individual conditions of the adjacent teeth and the entire set of teeth.

If a tooth restoration, e.g. a crown, is to be manufactured, the tooth color to be achieved is customarily determined by means of a comparison of an analogous, natural tooth with a specimen tooth or with a color platelet. The manufacturer of the specimen teeth collates the tooth colors offered by him into a catalog which is usually called a color ring. The specimen teeth or color platelets are documented in adjacent delimited areas with neck material, dentin material and enamel material. The combination of these three materials on each specimen tooth is determined by the manufacturer, as is the available selection of tooth colors. A dentist can therefore only select a specimen tooth whose color is the most similar to the natural tooth of the patient.

The combination of the color tones of the dental neck, the dentin and the enamel are not reproducible for the dentist and the dental technician. In addition, inclusions of color, transparency effects, individual shadings and color peculiarities can not be comprehended. The tooth color effects frequently deviate from the color combination of the specimen. A dental technician reconstructs a restoration in the laboratory not in accordance with the peculiarities of the patient but rather in accordance with the abstract color patterns in front of him. An aesthetically satisfactory restoration is in most instances left to the experience of the dental technician, but for the most part to chance.

A great number of limiting conditions must be observed in the selection of the colors of a dental prosthesis.

First of all, the inherent color of the restoration, composed of the color tone, color intensity and color temperature is important. The spectral composition of the particular light source with which the restoration is illuminated plays a part. The natural tooth is not opaque but rather more or less translucent on its surface; for this reason, the transparencies and translucencies of the enamel and of the dentin should be taken into consideration. Light reflections result in bright spots and bright lines; therefore even the surface nature of a replacement tooth should agree with the surface of the adjacent teeth.

However, foreign colors of various origins also influence the selection of color. The color of the inner (pulp) and of the outer (gingiva, tongue, lip, cheek) soft parts in the vicinity of the tooth and the color of the adjacent hard tooth substances or restorations exert an influence. The surrounding buccal environment must also be taken into consideration; a drying out of the natural teeth has the result that they become brighter.

It is not possible with the previously known selection devices for tooth color to achieve a satisfactory result in a restoration, not even to mention an optimally functional and aesthetic dental prosthesis.

A metal carrier functions as support for the color-specimen tooth mass in polychromatic color rings, color plates or specimen teeth like those known e.g. from DE 34 29 927 A1 (HENNING), DE 35 03 084 A1 (HERRMANN) or DE 36 18 153 A1 (METHE). This metal influences the color of the specimen tooth by means of a foreign color shining from behind; such specimen systems are therefore not suitable for a restoration in full ceramics. The burning on of color specimens onto metal substrates also causes a loss of transparency and translucency and brings about an opacity; a restored tooth constructed according to such a specimen is therefore not lifelike.

In the case of polychromatic color rings, several colors are deposited onto a single specimen, to wit, the colors of the compartments of enamel, dentin and dental neck. The colors of the compartments can therefore not be indicated individually but rather only in the combination determined by the manufacturer.

It is not possible to comprehend the various individual colors or colors of an individual tooth. It is not at all possible to seek out the color shade of individual inclusions of color in the tooth. Finally, there is no way in the case of the known color rings to supply the dental technician with data about the transparency and the translucency of a tooth.

In the known specimens, the base color is the base color of the dentin. The colors of the enamel and of the dental neck are layered thereover in an undefined thickness; and therefore, their color can not be reproduced in an unambiguous manner at a later date.

In general, the layer thickness of the color specimens is selected too high and addition, inhomogeneous. This results in erroneous evaluations when seeking out a color specimen because the color intensity and color shade are also dependent on the layer thickness. Thus, a shift in color can take place because individual wavelengths are reabsorbed or reflected in the specimen itself. The result can be a gray effect. This is brought about by means of a layering of a series of colors which result in a subtractive color mixture.

Most of the known color specimens are built up in a manner similar to a tooth. However, such a specimen can not be placed areally (i.e. contiguous with an exposed surface) on a tooth but rather there is a relatively large space between the specimen and the object, the tooth. The selection result is falsified by colors present in the vicinity because uncontrolled shining phenomena of light and color occur. The seeking out of a proper color is also made more difficult by the optical isolation between the specimen and the tooth because air has a refractive index of approximately n=1 and on the other hand a tooth and color specimen exhibit a refractive index of n=1.5 to 1.8.

Not only the size and the form but also the inflexible fastening of the specimen to a probe oppose an orderly determination of color. For this reason too a specimen can not be placed areally on a tooth. In the case of a few polychromatic specimen systems, even the color of a single compartment is greater than a natural tooth. The bulkiness of the specimens often makes their handling difficult for the user too.

As a result of the specified disadvantages, an "exact" seeking of the color requires far too much time. However, the eye adapts already after a quite short time and adjusts to the light conditions and the colors in the vicinity of the tooth. After the eye has adapted to a wavelength range, the "separating sharpness" of the perception of color in this wavelength range decreases sharply. The consequence thereof is the fact that the color is improperly selected.

Many color rings also suffer from the defect that different masses are used in the color specimens than are used subsequently in the restoration.

Monochromatic color rings come either as intensive color wheels or as ball color systems. Monochromatic color rings are known e.g. from DE 35 17 344 A1 (KRASS), DE 37 13 491 A1 (BOON) and EU 234 945 A2 (FORSYTH).

In the case of intensive color wheels, intensive colors serve for a fine tuning of base colors which had been roughly determined previously. Intensive colors are selected thereby which are intermingled with the normal tooth color. The difficulties already described above occur here too.

There is no possibility of precisely determining the total color impression, it is not possible to indicate the translucency and the transparency and also, the color of individual compartments can not be determined in a reproducible manner.

It is difficult for the user to precisely indicate the intensive colors for an individual color mixture.

In the case of intensive color wheels, no original masses are available in the mixing ratio used later.

The color specimens are burned onto an opaque carrier of plastic or metal. This results again in an influencing of color by the foreign color of the carrier shining through.

In the case of ball color systems, an areal placing of the color specimen on a tooth is totally impossible on account of the awkward shaping. Both the great average distance of the ball from the tooth as well as the punctiform contact of the specimen render a direct comparison of the color specimen with the tooth difficult. The color specimen is not only isolated very well optically from the tooth but it is also chromatically separated by means of shining from many different sources. The "correct" color is therefore practically impossible to find.

There is also no possibility of determining the transparency effect in ball color systems.

The complicated handling of such systems requires no further comment. The color rings which operate with templates like those known e.g. from DE 26 41 740 C2 (WIENAND) or EU 01 47 232 B1 (HALL) are particularly disadvantageous. The user must look through a window of a colored template onto the tooth and is supposed to compare the tooth color with the color of the template. Even the handling involving a living object, namely, a human patient, is not simple. A correct determination of color is not possible on account of the great distance of the specimen from the tooth and on account of the shadow effect of the frame-shaped specimen.

Moreover, the eye of the tester tends to concentrate on the larger colored area of the template frame than on the small window and is thus involuntarily deflected and deceived chromatically.

DE 35 23 982 A1 (MÜHLBAUER) involves the optical coupling of different layers of a color specimen for the adjustment of color in the repair of dental prostheses. To this end, an optical coupling liquid is introduced between the facing surfaces of adjacent layers. DE 35 23 982 A1 is relative to work performed in the dental laboratory but not to work performed in the mouth of a patient. This publication is concerned with the layered building up of color specimens, more precisely, with the building up of the layering (as regards the color) of artificial teeth. The use of optocoupling liquid between a color specimen element and the natural tooth surface in the mouth of a patient is not described by MÜhlbauer.

The initially mentioned apparatus for selecting a tooth color, is known from DE 37 31 254 A1 (ZFE). The color specimens known from this publication are on the order of magnitude of a complete tooth. The color specimens shown in this publication are curved in such a manner that an areal contact of the color specimens on the tooth, that is, on that (exposed) part of the tooth which is generally used for a color test, is not possible. As is already known from the state of the art, the color specimen taught in this publication also consists of a combination of colors, determined by the manufacturer, of differing tooth compartments (enamel, dentin and dental neck colors). For the rest, the carrier known from this publication for the color specimen consists of metal and only the outer, stained layer provided for the selection of color consists of facing mass.

SUMMARY OF THE INVENTION

The present invention is concerned with the problem of being able to adapt the color or the color distribution of a dental prosthesis to the particular structural conditions of the patient in an exact manner.

This problem is overcome by the present invention in which an apparatus for the selection of a tooth color for the manufacture of dental prostheses. The present invention comprises a platelet color specimen with at least one lateral edge concavely curved toward a central region of the platelet color specimen and at least one color specimen on the order of magnitude of the width of a tooth. This color specimen is shaped in such a manner that it can be placed areally against a tooth, more precisely, against the parts of the teeth which are generally used for a color comparison.

In addition thereto or alternatively thereto, the above-mentioned problem is also solved in that a color specimen exhibits only a single color corresponding to one tooth compartment (enamel, dentin or dental neck).

Furthermore the color specimens comprise an outer, stained layer consisting of facing material which is applied onto a carrier element and is intended for the selection of color and that the carrier element is also built up from the facing material.

The preceding invention has the advantage that the color specimen can be placed contiguous with a surface or edge of any exposed linear tooth areas of each tooth without a problematic intermediary space remaining. It can be considered a further advantage that the color of each tooth compartment can be determined by itself, namely, by means of a comparison with a color specimen suitable for it. Furthermore, the color-specimen platelets are manufactured of the same materials as the subsequent restoration; and therefore, are free of metal or other foreign substances.

Of further advantage to the user is that the carrier element is curved approximately like an umbrella, and is designed in an approximately triangular shape with the sides of the triangle concavely curved. In addition, the color-specimen platelet is approximately as wide as a tooth. These features make it possible to place the color specimen closely against any desired spot of each individual tooth, and to determine the color of the tooth rapidly without a disturbing and undesired shining phenomena. Moreover, it is also possible to exactly determine the color of individual inclusions or shadings in a simple manner by placing a corner of a triangle on a tooth.

According to the invention, the handling of the color-specimen platelets is also designed to be advantageous. Only a small ball which is connected to the platelet so as to form a single piece functions a connecting element between the platelet and a holding element. As a result thereof, the platelet can pivot in all directions on the holding element and can be readily placed against all teeth, especially against the back teeth and against the back side of the incisors for a determination of color.

The design of the connecting element, which is onepiece with the platelet, together with the glass-clear, transparent holding element, has the further advantage that any shining of foreign colors onto the color specimen is avoided since no foreign material is present on the color specimen, and the holding element is color-neutral. The same light sources act on the color specimen as on the object to be tested, the tooth, which makes a ready and precise determination of color possible.

A considerable advantage of the apparatus of the invention resides in the fact that the color-specimen platelets are manufactured homogeneously from a material of the same tooth-specimen color.

The tooth-specimen color is added section-by-section in a defined degree of transparency material and there are linearly flowing transitions with an increasing component of transparency material. As a result thereof, not only the correct tooth color but also the proper degree of transparency can be determined at each point of each tooth. Naturally, such a determination of color and transparency can also be readily carried out for inclusions and colored areas of a tooth on account of the advantageous form of the color-specimen platelet of the invention.

The exact determination of color is simplified even more by virtue of the fact that even the surface of the triangular color-specimen platelet is worked in the same manner, that is e.g. polished, as the intended restoration. For the rest, the thickness of the color-specimen platelet corresponds to the average processing thickness of dental restorations consisting e.g. of ceramics and plastic, which further increases the accuracy of the determination of color.

According to the invention, the colors of the dentin and of the enamel can be determined separately from one another, namely, with the aid of two sets of color specimens.

An additional color-specimen platelet serves to determine the opacity and receives a transition from a glass-clear transparent material to an opaque material.

Although there is a practical exclusion of light between the color-specimen platelets of the invention and the tooth during usage, the intermediary medium, air, between the tooth and the ceramic color specimen can be improved even more by adding in an optically adjusted liquid or gel-like medium, e.g. immersion oil. The liquid or gel functions as a light coupler. Its refractive index is selected so as to correspond to the refractive index of the tooth and of the restoration material.

The design in accordance with the invention of the probe which functions as a handle in conjunction with the color-specimen platelet not only makes possible a simple handling of the apparatus even in the area of the lateral teeth, but also allow rapid platelet replacement. In addition, the used platelets can be sterilized separately from the handle. It is sufficient when selecting a tooth color specimen to use a single handle in spite of several color-specimen platelets.

Since the color-specimen platelets consist e.g. of a ceramic mass or e.g. of plastic, they can not only be disinfected but even sterilized as often as desired without danger.

It is also advantageous to keep the storage container in a color complementary to the tooth colors to be determined. This makes it possible to sensitize the eye of the dentist in an optimum fashion before and during the selection of color and the determination of transparency, and prevents a premature adaptation of the receptor, the eye.

Other features and advantages result from the description of an embodiment in conjunction with the drawings, which show an embodiment in schematic fashion. The features can be realized and/or can be essential for the invention either individually or in any desired combination.

The invention is not limited to the embodiment but extends to all variations and designs which are covered by the claims and the disclosed features.

Embodiments of the invention are shown in the drawings and are described in more detail in the following description.

Figure 1:
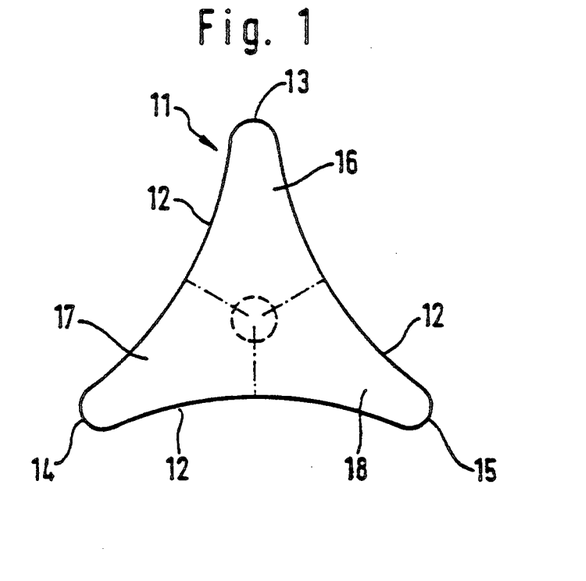
FIG. 1 shows a top view of a color-specimen platelet in accordance with the present invention.

FIG. 1 shows a color-specimen platelet 11 in schematic fashion. The color-specimen platelet has roughly the form of an equilateral triangle; however, sides 12 of the triangle are curved concavely inward and apices 13,14,15 are rounded. The surface of platelet 11 visible in FIG. 1 is divided into three areas 16,17,18 which merge into each other.

DESCRIPTION OF THE PREFERRED EMBODIMENTS

According to the invention, the system of the apparatus comprises three series of color-specimen platelets. The platelets are homogeneously manufactured from a material of a monochromatic specimen color in accordance with the standardized tooth colors specified by the manufacturer.

In the first color-specimen series, the first color area 16 is built up e.g. from a pure dentin color. In the second area 17 a transparency mass is intermixed with the dentin color. The mixing ratio is approximately two thirds dentin material and one third transparency material. In the third area 18 the mixing ratio is approximately one third dentin material and two thirds transparency material. The three areas 16,17,18 are not sharply delineated from each other but rather the color transitions run in a linearly flowing manner from one area to another area. The above-indicated mixing ratio applies only to the particular apices 13,14 and 14—thus, the triangle apices 13,14,15 can be considered as the center of areas 16,17,18. A pure enamel color is used in the second series of color specimens. The first area 16 contains the pure enamel material, the second area 17 consists of approximately two thirds enamel material and one third transparency material and the third area 18 contains one third enamel material and two thirds transparency material. The color transitions also flow in a linear fashion here. Only one platelet is provided for the third color series, which could be designated as a transparency material platelet. The first area 16 is manufactured from glass-clear transparency material, the second area 17 contains a mixture of equal parts of transparency material and opaque material and therefore appears to be clear grey and opaque material is used in the third area 18.

Figure 2:
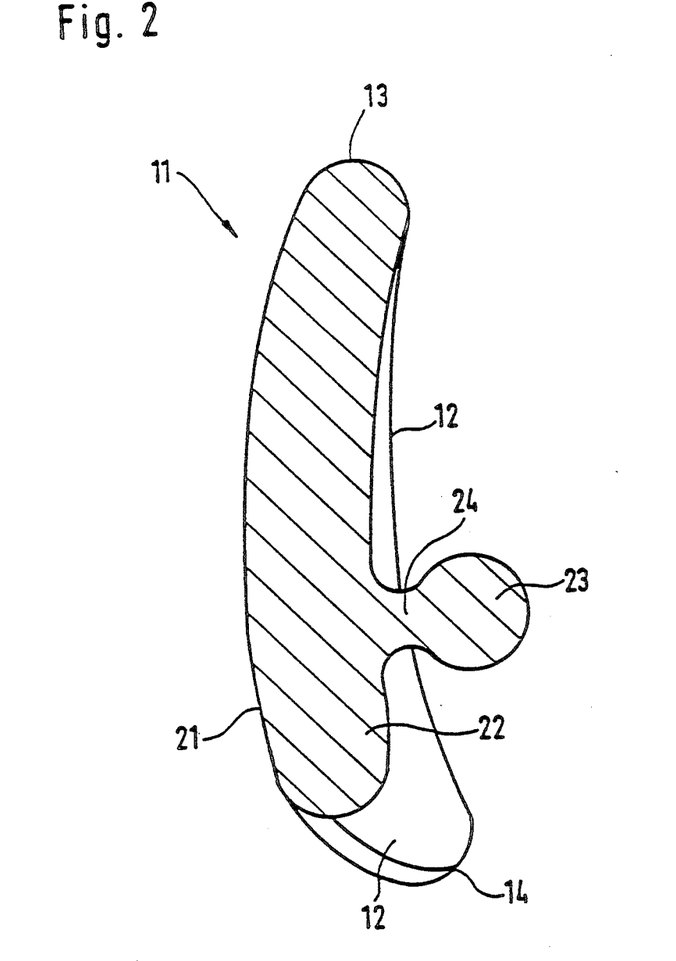
FIG. 2 shows a sectional side view of the platelet of FIG. 1.

FIG. 2 shows a section through color-specimen platelet 11. The same parts are provided with the same reference numerals, e.g. the triangle apices 13,14 visible in section and the partially visible lower triangle side 12. The construction of color-specimen platelet 11 can be seen in section. Carrier element 22 is curved in a manner similar to a flat umbrella in a spherical segment and exhibits a convex outer side 21.

A first part of a connecting element is shown centrally on the concave side of carrier element 22, namely, a spherical head 23 connected via neck 24 to carrier element 22. Head 23 and neck 24 are designed in one piece with carrier element 22 and consist of the same material and are of the same color. The same material is used which is also intended for the subsequent tooth restoration.

The size of the platelet shown in FIGS. 1,2 is approximately on the order of magnitude on one tooth width. One triangle side 12 is therefore approximately eight to 10 millimeters long. The entire thickness of a platelet 22 corresponds approximately to the thickness of a tooth-colored restoration, that is, approximately one to two millimeters.

Figure 3:
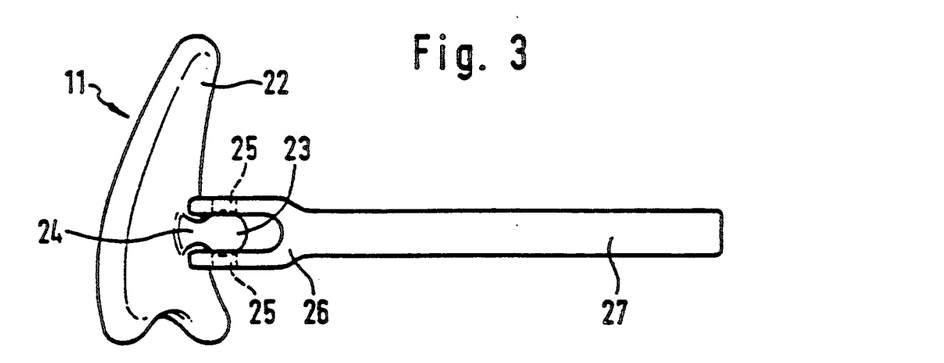
FIG. 3 shows a color-specimen platelet in conjunction with a holding element, viewed from the side.

FIG. 3 shows a complete apparatus like that guided by the user onto the teeth of a patient. How spherical head 23, the one part of the connecting element, snaps into recesses 25 in a forked holder 26 of holding element 27 is not shown true to scale. Forked holder 26 with recesses 25 represents the other part of the fastening element. Holding element 27 with fork 26 is preferably manufactured from transparent acrylic glass and polished. This measure avoids foreign shining phenomena and disturbing reflections of color when selecting the color. As can be readily recognized, color platelet 11 can be adjusted with the aid of spherical head 23 in fork 26 in almost all directions. In this manner, the user of the apparatus in accordance with the invention can place color-specimen platelet 11 in the patient's mouth on all teeth, both on their outer side and on their inner side, without difficulty.

Figure 4:
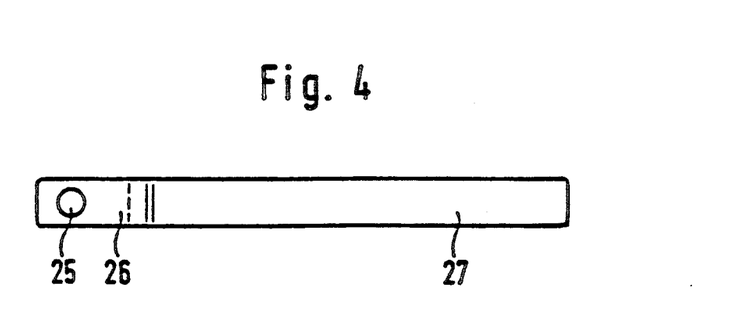
FIG. 4 shows a top view of the holding element.

FIG. 4 shows another view of holding element 27 with fork 26 in a schematic fashion which is not true to scale.

Figure 5:
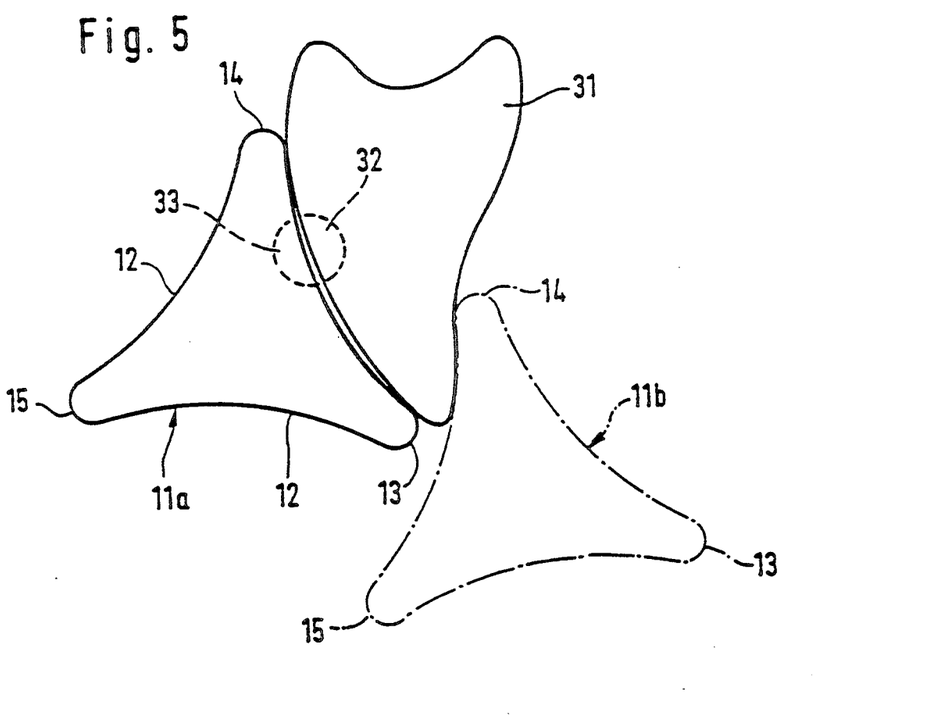
FIGS. 5 to 7 show applications of the color-specimen platelet to an incisor, viewed from the side, from above and from the front respectively.

FIG. 5 shows an incisor 31 in a side view. Two of the countless possibilities of placing a tooth color specimen platelet 11a or 11b against tooth 31 are indicated. It is assumed as example, that the user wishes to examine a color spot 32 on tooth 31. First of all, he determines the color from his color catalog (assortment of specimen platelets) which is appropriate for the tooth spot. Then, he places the color platelet which was determined to be appropriate against the tooth, as shown in FIG. 5, in order to determine the ratio of tooth color to transparency material. In the example shown, he has found the optimum ratio at a certain position of side 12 between apices 13 and 14. It can also be seen from the example of FIG. 5 that the radius of curvature of side 12 is designed in such a manner that a platelet can be placed on practically all tooth surfaces. FIG. 5 also indicates as a further example how the one apex 14 of platelet 11 is placed on the lingual side of tooth 31 for color testing.

Figure 6:
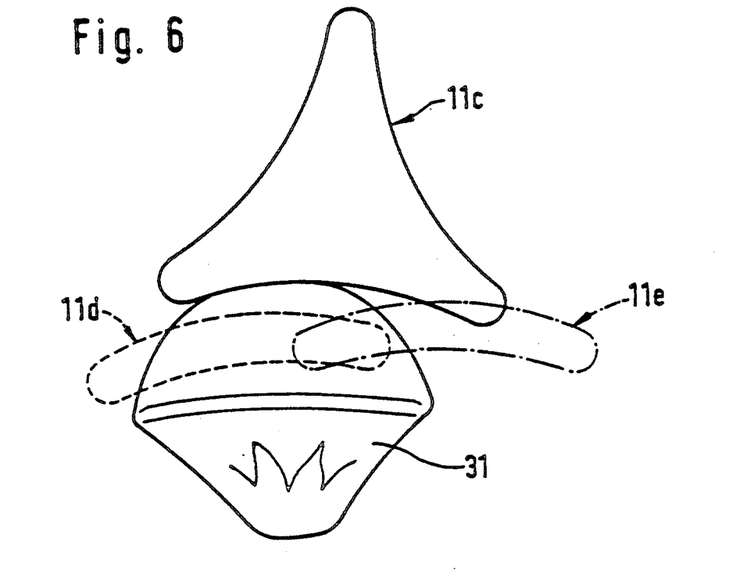

FIG. 6 shows a few embodiments of a color test in which an incisor is sketched from above. Three possible placements of a specimen platelet 11c, 11d, and 11e are shown.

Figure 7:
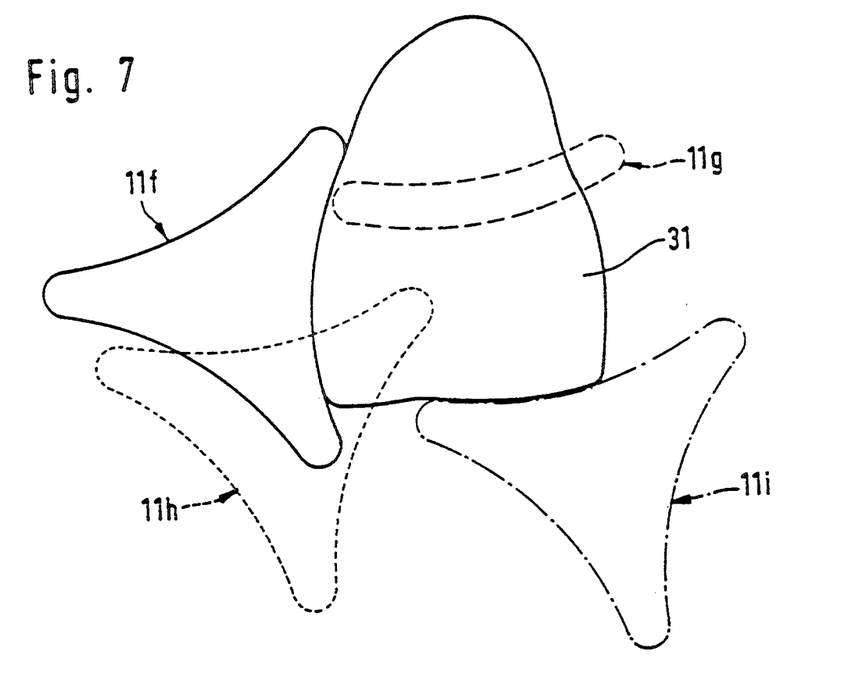

FIG. 7 shows four possible placements for a platelet 11f, 11g, 11h and 11i on an incisor 31 which can be seen in a front view.

Figure 8:
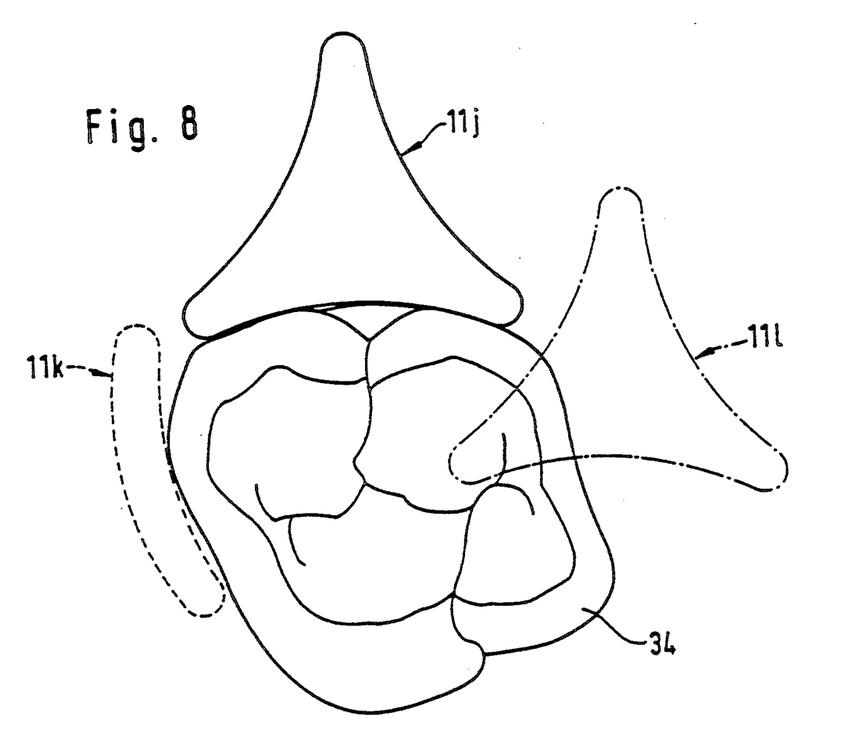
FIGS. 8 to 10 show the application of a color-specimen platelet to a molar, viewed from above, from the side and from the front respectively.
Figure 9:
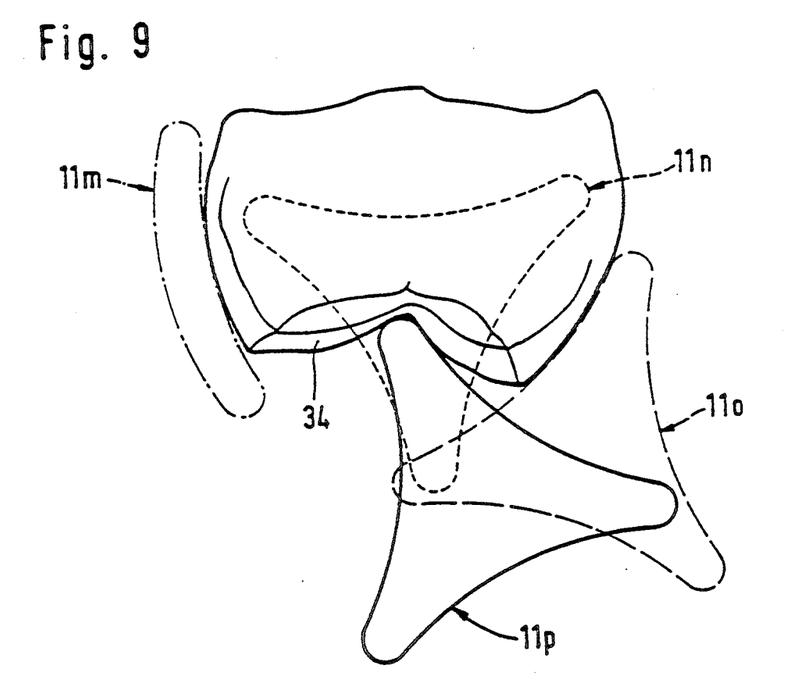
Figure 10:
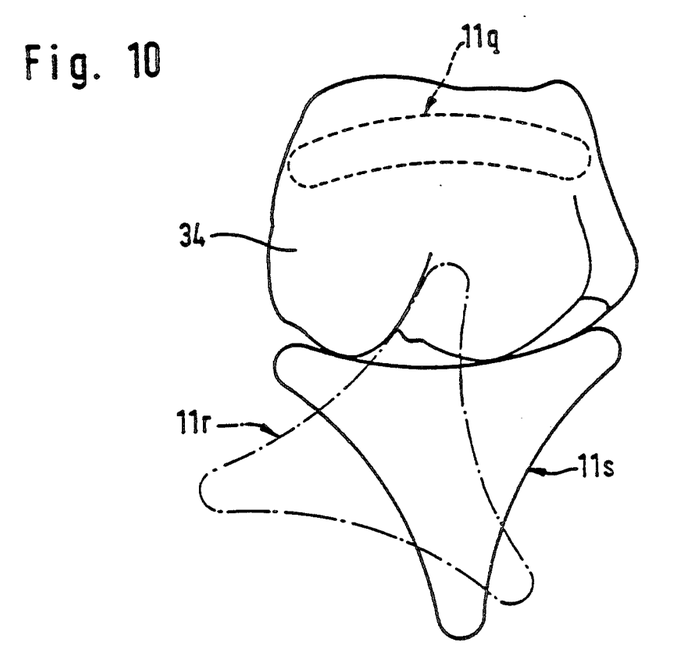

FIGS. 8,9,10 show numerous possibilities of placement of a platelet 11j-11s in conjunction with a molar 34.

FIGS. 5 to 10 do not show that a drop of optical coupling liquid can be brought with advantage between platelet 11 and teeth 31 and 34 in order to avoid an optical interruption, even if ever so small. The liquid (e.g. immersion oil) functions as light coupler and has the same refractive index as the natural tooth and the material of the prosthesis, namely, approximately n=1.5 ... 1.8. Erroneous interpretations of the tooth color can be completely excluded by means of the optical exclusion of light achieved in this manner.

The platelets are stored prior to being used in a container which is maintained in a color complementary to the average color of the platelets. Such a complementary color is in the blue range and has a wavelength of approximately 480–490 nm. This can circumvent an adaptation or a premature readaptation of the eyes of the user to the tooth colors.

Note also that connecting elements 23,26 of the invention also permit platelets 11 to be rapidly replaced when seeking an optimum color. This has the additional pleasant side effect that for each color test a plurality of plates but only a single handle 27 is required, and has to be sterilized afterwards.

Figure 11:
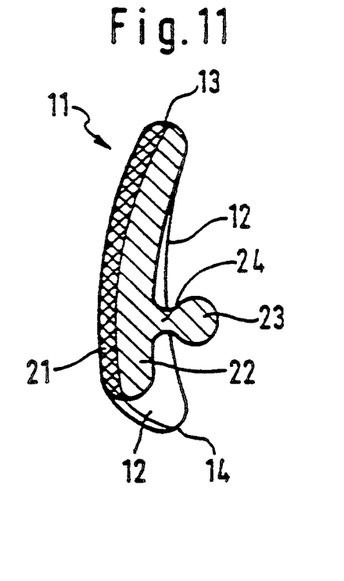
FIG. 11 shows a color-specimen platelet in accordance with the invention viewed from the side in partial section.

FIG. 11 shows a variant in which a layer consisting e.g. of ceramics and/or plastic is applied as convex area 21 onto a carrier element 22 manufactured from any desired material. This layer 21 exhibits the qualities of color, transparency and opaqueness already described above.

I claim:

1. An apparatus for selecting tooth color of a dental prosthesis comprising a platelet color specimen having at least one lateral edge concavely curved toward a central region of the platelet color specimen; the platelet color specimen having a shape which permits placement contiguous with any exposed surface of a tooth.

2. An apparatus according to claim 1, wherein the platelet color specimen has a generally triangular contour.

3. An apparatus according to claim 2, wherein the generally triangular contour of the platelet color specimen has rounded apices.

4. An apparatus according to claim 2, wherein at least one side of the generally triangular contour of the platelet color specimen has a length on the order of magnitude of a width of a tooth.

5. An apparatus according to claim 1, wherein the platelet color specimen has a generally equilateral triangular contour.

6. An apparatus according to claim 1, wherein the platelet color specimen's contour approximates a triangle having sides concavely curved toward a central region of the platelet color specimen.

7. An apparatus according to claim 1, wherein the platelet color specimen has a convex front surface.

8. An apparatus according to claim 7, wherein the platelet color specimen has a concave back surface.

9. An apparatus according to claim 8, wherein the platelet color specimen has a thickness on the order of magnitude of an average processing thickness of a dental prosthesis.

10. An apparatus according to claim 1, wherein the platelet color specimen has a single color corresponding to one of enamel, dentin and dental neck.

11. An apparatus corresponding to claim 10, wherein the platelet color specimen comprises:
a carrier element composed of a facing material; and
an outer, stain layer, of the facing material applied to the carrier element for selection of dental prostheses color.

12. An apparatus according to claim 11, wherein the facing material is the same material as used in manufacturing the dental prostheses.

13. An apparatus according to claim 12, wherein the facing material is at least one of ceramic material, plastic material, and a tooth colored restoration material.

14. An apparatus according to claim 1, further comprising:
a holding device; and
the platelet color specimen comprises a connecting means for connecting the platelet color specimen to the holding device wherein the platelet color specimen can be adjusted in a multidirectional manner.

15. An apparatus according to claim 14, wherein:
the connecting means comprises a spherical head connected to the platelet color specimen via a neck; and
the holding device comprises a forked holder with tines at one end, the forked holder having recesses on the inner sides of the tines for engagement of the spherical head.

16. An apparatus according to claim 15, wherein the spherical head is fastened via the neck to a back surface of the platelet color specimen.

17. An apparatus according to claim 16, wherein the spherical head is located at the center of the back surface of the platelet color specimen.

18. An apparatus according to claim 15, wherein the spherical head with neck has a height greater than the thickness of the platelet color specimen.

19. An apparatus according to claim 14, wherein the connecting means is composed of facing material.

20. An apparatus according to claim 14, wherein the connecting means is integrally formed with the color specimen.

21. An apparatus according to claim 14, wherein the holding device is manufactured from glass-clear transparent material.

22. An apparatus according to claim 14, wherein the platelet color specimen is manufactured from one of dental prosthesis material and transparent material.

23. An apparatus according to claim 1, wherein a front surface of the platelet color specimen is treated in the same manner as a manufactured dental prosthesis.

24. An apparatus according to claim 1, wherein the platelet color specimen is composed of specimen color and transparent material.

25. An apparatus according to claim 24, wherein the platelet color specimen is further composed of an opaque material.

26. An apparatus according to claim 1, wherein the platelet color specimen comprises several areas, each with a different mixing ratio of one of specimen color and transparent material, and transparent material and opaque material.

27. An apparatus according to claim 26, wherein the mixing ratio changes in a linearly flowing manner from one area to another area.

28. An apparatus according to claim 27, wherein:
the platelet color specimen has a generally triangular contour, and has three areas arranged in such a manner that the center of a mixing ratio is located essentially in one of the apices of the generally triangular contour.

29. An apparatus according to claim 26, wherein the platelet color specimen comprises three areas:
a first area containing specimen color, a second area containing approximately two thirds specimen color and one third transparent material, and a third area containing approximately one third specimen color and two thirds transparent material.

30. An apparatus according to claim 26, wherein the platelet color specimen comprise three areas:
a first area containing transparent material, a second area containing approximately equal portions of transparent material and opaque material, and a third area containing pure opaque material.

31. An apparatus according to claim 1, further comprising a light-coupler liquid added in between the platelet color specimen and a tooth, the light-coupler liquid having a refractive index similar to that of the tooth and the platelet color specimen.

32. An apparatus according to claim 1, further comprising a storage container for storing a plurality of platelet color specimens; the storage container having inner walls exhibiting color with a wavelength of 480 to 490 nm.

33. An apparatus for selecting tooth color of a dental prosthesis comprising a platelet color specimen having a generally triangular contour with at least one lateral edge concavely curved towards a center region of the platelet color specimen; the platelet color specimen having a shape which permits placement contiguous with any exposed portion of a tooth.

34. An apparatus for selecting tooth color of a dental prosthesis comprising a platelet color specimen having at least one lateral edge concavely curved towards a center region of the platelet color specimen; the platelet color specimen having a shape which permits placement contiguous with any exposed edge of a tooth.

35. An apparatus for selecting tooth color of a dental prosthesis comprising a platelet color specimen having at least one lateral edge concavely curved towards a center region of the platelet color specimen; the platelet color specimen having a shape which permits placement contiguous with any exposed surface and edge of a tooth.

* * * * *